United States Patent [19]

Whitsell

[11] Patent Number: Plant 5,299

[45] Date of Patent: Oct. 23, 1984

[54] AVOCADO TREE—'WHITSELL'

[75] Inventor: Robert H. Whitsell, Riverside, Calif.

[73] Assignee: The Regents of the University of California, Berkeley, Calif.

[21] Appl. No.: 467,627

[22] Filed: Feb. 18, 1983

[51] Int. Cl.[3] ..... A01H 5/03

[52] U.S. Cl. ..... Plt./44

[58] Field of Search ..... Plt./44

*Primary Examiner*—Robert E. Bagwill

*Attorney, Agent, or Firm*—Townsend and Townsend

[57] ABSTRACT

A new and distinct variety of avocado tree characterized by its smallness in size, high productivity, larger fruit than 'Hass' and handsome fruit color.

2 Drawing Figures

DESCRIPTION

This invention relates to a new and distinct variety of avocado tree designated as 'Whitsell' and tested as selection 23/8/29.

'Whitsell' is a seedling selection of the 'Hass' cultivar and has been propagated asexually by T-budding, whip-grafting, saddle-grafting and saw-kerf grafting at the University of California, Riverside and South Coast Field Station facilities in Southern California where the variety has been tested.

Figure 1:
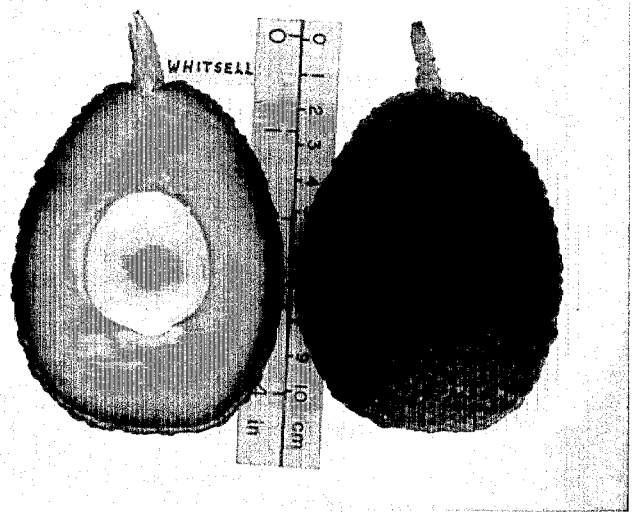
FIG. 1 shows typical fruiting characteristics of the tree.
Figure 2:
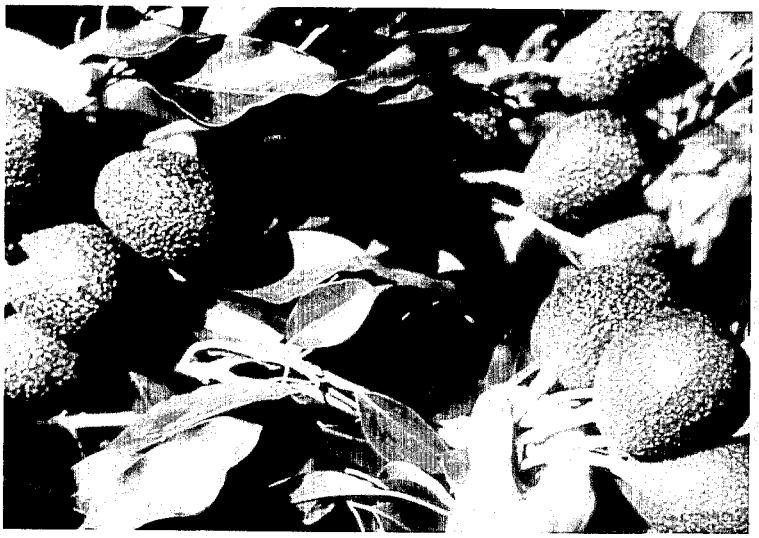
FIG. 2 shows the heavy fruit-set ability typical of the tree.

'Whitsell' has three primary distinguishing characteristics. First, its tree is smaller than 'Hass' which results in reduced picking costs and lessened tendency to suffer wind damage. Second, its production per acre is appreciably higher than 'Hass'; about twenty-five to forty percent from experience to date, based chiefly on several trees observed over several years at the testing areas. Third, the fruit size of 'Whitsell' is a little larger than 'Hass' which produces many fruits too small for the preferred commercial market in most years. Moreover, 'Whitsell' is of "B" flowering type, making it a better pollinator for the major "A"-type commercial cultivars: 'Hass', 'Pinkerton', and 'Reed'. Like 'Hass' production of 'Whitsell' alternates.

Probably the chief disadvantage of 'Whitsell' is its development of more obvious russeting or corking of the skin, especially late in its season. However, the fruit is a handsome deep green and more attractive than such commercial cultivars as 'Pinkerton'.

No resistance of 'Whitsell' is known to the few insects which are rarely a problem to avocado trees, nor to Verticillium wilt, the Black-streak disease or the Sunblotch viroid. Resistance to Phytophthora is a property of the rootstock and not the scion top. In resistance to the physiological disease of freezing injury, 'Whitsell' rates "tender" and is about comparable to the 'Hass' standard.

It is impossible to assign very meaningful distinctions of the new variety based upon color. With reference to the Horticulture Colour Charts (issued by Wilson Colour Ltd. in collaboration with The Royal Horticultural Society) typical fruit of 'Whitsell' has the background skin color designated as Parsley Green, oo962 (Repertoire, Vert barbedienne 287/1). The basic green skin color not only varies of itself, but is flecked with numerous tiny islands of varying yellowish shades. Moreover, the two halves of the fruit usually differ in average color. Each average color differs according to the time of fruit-set (which may vary widely on a tree), the degree of maturity, geographic location, and possibly other factors. Nevertheless, the basic background skin color above-identified is the most consistent color feature of the fruit of this variety.

Trees and foliage

'Whitsell', as in the case of most avocado cultivars, does not have distinctive foliage and cannot consistently be distinguished from 'Hass' on the basis of leaf, flower, or limb traits. In tree form 'Whitsell' is erratic and irregular in branch outline and fairly distinctive among avocados. It is semi-dwarf, very dense with moderate vigor. Leaves are smaller and deeper green than 'Hass'.

Fruit

Ovate to pear, shorter and thicker than 1 Hass'. About 300 grams per average. Dark green, rough skin, thicker than 'Hass' but pliable. Fine russet speckle on blossom end, becoming more pronounced and general as the fruit matures. Season is about April through September. Flesh less rich yellow than 'Hass'. Flavor less nutty than 'Hass', "very good". Seed even smaller than 'Hass'. Very heavy production in alternate years.

1. The new and distinct variety of avocado tree herein described and illustrated and identified by the characteristics enumerated above.

* * * * *